United States Patent
Murthy et al.

(10) Patent No.: US 11,446,279 B2
(45) Date of Patent: Sep. 20, 2022

(54) AROMATIC 2-NITROSULFONYL FLUORIDE ANTIBIOTICS AND METHODS OF USE THEREOF

(71) Applicant: The Regents of the University of California, Oakland, CA (US)

(72) Inventors: Niren Murthy, Berkeley, CA (US); Corinne Sadlowski, Berkeley, CA (US); Bora Park, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 151 days.

(21) Appl. No.: 16/618,952

(22) PCT Filed: Jun. 27, 2018

(86) PCT No.: PCT/US2018/039851
§ 371 (c)(1),
(2) Date: Dec. 3, 2019

(87) PCT Pub. No.: WO2019/006025
PCT Pub. Date: Jan. 3, 2019

(65) Prior Publication Data
US 2020/0085785 A1    Mar. 19, 2020

Related U.S. Application Data

(60) Provisional application No. 62/526,914, filed on Jun. 29, 2017.

(51) Int. Cl.
| | |
|---|---|
| A61K 31/381 | (2006.01) |
| A61P 31/04 | (2006.01) |
| A61K 31/10 | (2006.01) |
| A61K 31/4178 | (2006.01) |
| A61K 45/06 | (2006.01) |
| C07D 333/44 | (2006.01) |

(52) U.S. Cl.
CPC ............ *A61K 31/381* (2013.01); *A61K 31/10* (2013.01); *A61K 31/4178* (2013.01); *A61K 45/06* (2013.01); *A61P 31/04* (2018.01); *C07D 333/44* (2013.01)

(58) Field of Classification Search
None
See application file for complete search history.

(56) References Cited

U.S. PATENT DOCUMENTS

| | | |
|---|---|---|
| 2004/0087568 A1 | 5/2004 | Huang et al. |
| 2005/0201999 A1 | 9/2005 | Taylor et al. |
| 2010/0022584 A1 | 1/2010 | Kenyon et al. |
| 2015/0071904 A1 | 3/2015 | Collins et al. |
| 2015/0104846 A1* | 4/2015 | Kataoka ........... G01N 33/57438 435/184 |

OTHER PUBLICATIONS

Patani et al. "Bioisosterism: A Rational Approach in Drug Design" Chemical Reviews, 1996, vol. 96, pp. 3147-3176.*
Pubchem, Substance Record for SID 313624630, Available Date: Jun. 14, 2016 [retrieved on Aug. 7, 2018]. Retrieved from the Internet: <URL: https://pubchem .ncbi.nlm.nih.gov/substance/ 313624630>.

* cited by examiner

*Primary Examiner* — Joseph R Kosack
(74) *Attorney, Agent, or Firm* — Bozicevic Field & Francis, LLP; Paula A. Borden; Mandar A. Joshi

(57) ABSTRACT

Aspects of the present disclosure include antibacterial aromatic sulfonyl fluoride agents. The subject aromatic sulfonyl fluoride agents have a pharmacophore that can provide for potent antibacterial activity. The subject agents are compounds including an aromatic group substituted with a sulfonyl fluoride warhead group and an electron withdrawing group. The subject agents find use in a variety of antibiotic applications. In some cases, the subject agents find use in methods of treating bacterial infections in a subject. Also provided are pharmaceutical compositions and kits that find use in practicing the subject methods.

16 Claims, 1 Drawing Sheet

AROMATIC 2-NITROSULFONYL FLUORIDE ANTIBIOTICS AND METHODS OF USE THEREOF

CROSS-REFERENCE

This application claims the benefit of U.S. Provisional Patent Application No. 62/526,914, filed Jun. 29, 2017, which application is incorporated herein by reference in its entirety.

STATEMENT REGARDING FEDERALLY SPONSORED RESEARCH

This invention was made with government support under Grant No. AI17064 awarded by the National Institutes of Health. The government has certain rights in the invention.

INTRODUCTION

Antibiotics are losing efficacy at an alarming rate, due to the rapid spread of drug-resistant bacteria and the slow rate at which new antibiotics are being developed. In the United States alone, at least 2 million people per year become infected with drug-resistant bacterial pathogens, and this number is much higher in developing nations such as China, Russia, Brazil, and India. Drug-resistant GNB have the potential to cause a public health care crisis if immediate action is not taken. In February 2017, the WHO issued a report in which they published the first ever list of antibiotic-resistant "Priority Pathogens", of which the "Priority 1" pathogens that are considered "Critical" include carbapenem-resistant *Acinetobacter baumanni, Pseudomonas aeruginosa*, and various Enterobacteriaceae, all of which are GNB. Additionally, the CDC has highlighted "Four Core Actions to Prevent Antibiotic Resistance", with one action being the need for alternative drug development.

Infections caused by drug-resistant Gram-negative bacteria (GNB) have quickly become a global problem in medicine and developing antibiotics has been challenging because of the onset of drug-resistant mechanisms and their low membrane permeability. Despite significant effort, no new classes of antibiotics have been clinically approved in the last 25 years and this deficiency has the potential to generate a public health crisis given that resistance to all known antibiotics will likely occur within the next 10-20 years.

A key challenge limiting the development of new drugs against GNBs is their low membrane permeability. GNBs have two membranes through which drugs must penetrate: an outer membrane (OM) and a cytoplasmic membrane (CM), and together these membranes prevent both hydrophilic and hydrophobic molecules from entering GNBs. Due to these membrane permeability limitations, numerous antibiotics have been developed against gram-positive bacteria have no efficacy against gram-negative bacteria. The development of pharmacophore scaffolds that are both permeable to GNBs and have antibacterial activity is of interest.

SUMMARY

Aspects of the present disclosure include antibacterial aromatic sulfonyl fluoride agents. The subject aromatic sulfonyl fluoride agents have a pharmacophore that can provide for potent antibacterial activity. The subject agents are compounds including an aromatic group substituted with a sulfonyl fluoride warhead group and an electron withdrawing group. The subject agents find use in a variety of antibiotic applications. In some cases, the subject agents find use in methods of treating bacterial infections in a subject. Also provided are pharmaceutical compositions and kits that find use in practicing the subject methods.

DEFINITIONS

Figure 1:
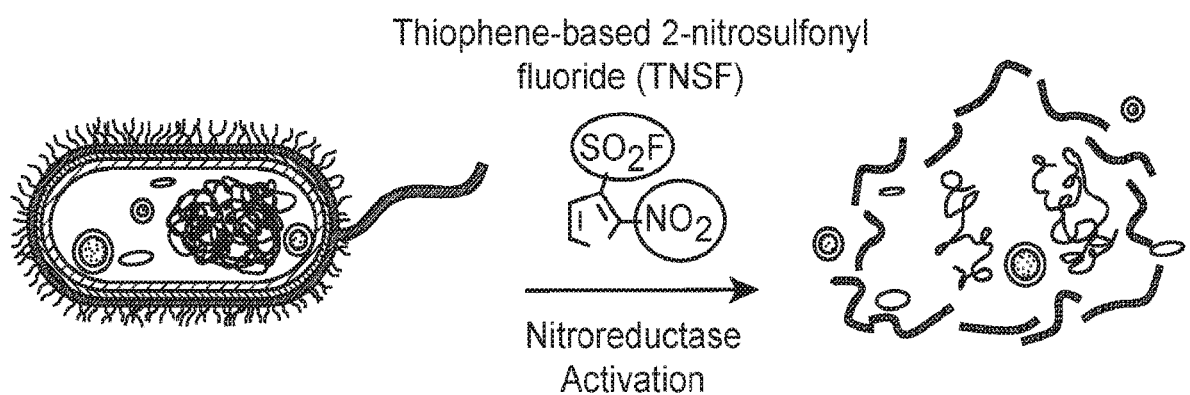
FIG. 1 depicts thiophene-based 2-nitrosulfonyl fluorides (TNSFs) as a class of pharmacophores for antibiotics. TNSFs react with proteins inside bacteria followed by nitroreductase (NR) activation to generate radical intermediates, leading to protein degradation and apoptosis.

"Alkyl" refers to monovalent saturated aliphatic hydrocarbyl groups having from 1 to 20 carbon atoms and such as 1 to 10 carbon atoms, or 1 to 6, or 1 to 5, or 1 to 4, or 1 to 3 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups having from 1 to 20 and in some cases, 1 to 10, or 1 to 6, or 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—$CH_2$—), ethylene (—$CH_2CH_2$—), n-propylene (—$CH_2CH_2CH_2$—), iso-propylene (—$CH_2CH(CH_3)$—), (—$C(CH_3)_2CH_2CH_2$—), (—$C(CH_3)_2CH_2C(O)$—), (—$C(CH_3)_2CH_2C(O)NH$—), (—$CH(CH_3)CH_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R is alkyl group as defined herein and R" is alkylene, alkenylene or alkynylene group as defined herein.

The term "alkaryl" or "aralkyl" refers to the groups-alkylene-aryl and-substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups-alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group-alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 20 carbon atoms and in some cases 2 to 10 carbon atoms, such as 2 to 7 carbon atoms, and having at least 1 and in some cases from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Allenyl" refers to straight chain or branched hydrocarbyl groups having from 2 to 20 carbon atoms and in some cases 2 to 10 carbon atoms, such as 2 to 7 carbon atoms and having a carbon atom having double bond unsaturation to each of its two adjacent carbon atoms. Included within this term are the stereo isomers or mixtures of these isomers.

The term "substituted allenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 20 carbon atoms and in some cases 2 to 10 carbon atoms, such as 2 to 7 carbon atoms, and having at least 1 and in some cases from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—

"Acylamino" refers to the groups —NR$^{20}$C(O)alkyl, —NR$^{20}$C(O)substituted alkyl, NR$^{20}$C(O)cycloalkyl, —NR$^{20}$C(O)substituted cycloalkyl, —NR$^{20}$C(O)cycloalkenyl, —NR$^{20}$C(O)substituted cycloalkenyl, —NR$^{20}$C(O) alkenyl, —NR$^{20}$C(O)substituted alkenyl, —NR$^{20}$C(O)alkynyl, —NR$^{20}$C(O)substituted alkynyl, —NR$^{20}$C(O)aryl, —NR$^{20}$C(O)substituted aryl, —NR$^{20}$C(O)heteroaryl, —NR$^{20}$C(O)substituted heteroaryl, —NR$^{20}$C(O)heterocyclic, and —NR$^{20}$C(O)substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{21}$C(O)NR$^{22}$R$^{23}$ where R$^{21}$, R$^{22}$, and R$^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —N$_3$.

"Carboxyl," "carboxy" or "carboxylate" refers to —CO$_2$H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond and in some cases from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The term "heteroaralkyl" refers to the groups-alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$-moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO— substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group —NO$_2$.

"Oxo" refers to the atom (=O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-$SO_2$—, phenyl-$SO_2$—, and 4-methylphenyl-$SO_2$—.

"Sulfonyloxy" refers to the group —$OSO_2$-alkyl, $OSO_2$-substituted alkyl, $OSO_2$-alkenyl, $OSO_2$-substituted alkenyl, $OSO_2$-cycloalkyl, $OSO_2$-substituted cycloalkyl, $OSO_2$-cycloalkenyl, $OSO_2$-substituted cylcoalkenyl, $OSO_2$-aryl, $OSO_2$-substituted aryl, $OSO_2$-heteroaryl, $OSO_2$-substituted heteroaryl, $OSO_2$-heterocyclic, and $OSO_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =$NR^{70}$, =N—$OR^{70}$, =$N_2$ or =S) on saturated carbon atoms in the specified group or radical are, unless otherwise specified, —$R^{60}$, halo, =O, —$OR^{70}$, —$SR^{70}$, —$NR^{80}R^{80}$, trihalomethyl, —CN, —OCN, —SCN, —NO, —$NO_2$, =$N_2$, —$N_3$, —$SO_2R^{70}$, —$SO_2O^-M^+$, —$SO_2OR^{70}$, —$OSO_2R^{70}$, —$OSO_2O^-M^+$, —$OSO_2OR^{70}$, —P(O)($O^-$)$_2$($M^+$)$_2$, —P(O)($OR^{70}$)$O^-M^+$, —P(O)($OR^{70}$)$_2$, —C(O)$R^{70}$, —C(S)$R^{70}$, —C($NR^{70}$)$R^{70}$, —C(O)O $M^+$, —C(O)$OR^{70}$, —C(S)$OR^{70}$, —C(O)$NR^{80}R^{80}$, —C($NR^{70}$)$NR^{80}R^{80}$, —OC(O)$R^{70}$, —OC(S)$R^{70}$, —OC(O)$O^-M^+$, —OC(O)$OR^{70}$, —OC(S)$OR^{70}$, —$NR^{70}$C(O)$R^{70}$, —$NR^{70}$C(S)$R^{70}$, —$NR^{70}CO_2^-M^+$, —$NR^{70}CO_2R^{70}$, —$NR^{70}$C(S)$OR^{70}$, —$NR^{70}$C(O)$NR^{80}R^{80}$, —$NR^{70}$C($NR^{70}$)$R^{70}$ and —$NR^{70}$C($NR^{70}$)$NR^{80}R^{80}$, where $R^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each $M^+$ is a counter ion with a positive charge. Each $M^+$ may independently be, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —$NR^{80}R^{80}$ is meant to include —$NH_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —$R^{60}$, halo, —$O^-M^+$, —$OR^{70}$, —$SR^{70}$, —$S^-M^+$, —$NR^{80}R^{80}$, trihalomethyl, —$CF_3$, —CN, —OCN, —SCN, —NO, —$NO_2$, —$N_3$, —$SO_2R^{70}$, —$SO_3^-$ $M^+$, —$SO_3R^{70}$, —$OSO_2R^{70}$, —$OSO_3^-M^+$, —$OSO_3R^{70}$, —$PO_3^{-2}(M^+)_2$, —P(O)($OR^{70}$)$O^-M^+$, —P(O)($OR^{70}$)$_2$, —C(O)$R^{70}$, —C(S)$R^{70}$, —C($NR^{70}$)$R^{70}$, —$CO_2^-M^+$, —$CO_2R^{70}$, —C(S)$OR^{70}$, —C(O)$NR^{80}R^{80}$, —C($NR^{70}$)$NR^{80}R^{80}$, —OC(O)$R^{70}$, —OC(S)$R^{70}$, —$OCO_2^-M^+$, —$OCO_2R^{70}$, —OC(S)$OR^{70}$, —$NR^{70}$C(O)$R^{70}$, —$NR^{70}$C(S) $R^{70}$, —$NR^{70}CO_2^-M^+$, —$NR^{70}CO_2R^{70}$, —$NR^{70}$C(S)$OR^{70}$, —$NR^{70}$C(O)$NR^{80}R^{80}$, —$NR^{70}$C($NR^{70}$)$R^{70}$ and —$NR^{70}$C($NR^{70}$)$NR^{80}R^{80}$, where $R^{60}$, $R^{70}$, $R^{80}$ and $M^+$ are as previously defined, provided that in case of substituted alkene or alkyne, the substituents are not —$O^-M^+$, —$OR^{70}$, —$SR^{70}$, or —$S^-M^+$.

In addition to the groups disclosed with respect to the individual terms herein, substituent groups for hydrogens on nitrogen atoms in "substituted" heteroalkyl and cycloheteroalkyl groups are, unless otherwise specified, —$R^{60}$, —$O^-M^+$, —$OR^{70}$, —$SR^{70}$, —$S^-M^+$, —$NR^{80}R^{80}$, trihalomethyl, —$CF_3$, —CN, —NO, —$NO_2$, —S(O)$_2R^{70}$, —S(O)$_2O^-M^+$, —S(O)$_2OR^{70}$, —OS(O)$_2R^{70}$, —OS(O)$_2O^-M^+$, —OS(O)$_2OR^{70}$, —P(O)($O^-$)$_2(M^+)_2$, —P(O)($OR^{70}$)$O^-M^+$, —P(O)($OR^{70}$)($OR^{70}$), —C(O)$R^{70}$, —C(S)$R^{70}$, —C($NR^{70}$)$R^{70}$, —C(O)$OR^{70}$, —C(S)$OR^{70}$, —C(O) $NR^{80}R^{80}$, —C($NR^{70}$)$NR^{80}R^{80}$, —OC(O)$R^{70}$, —OC(S)$R^{70}$, —OC(O)$OR^{70}$, —OC(S)$OR^{70}$, —$NR^{70}$C(O)$R^{70}$, —$NR^{70}$C (S)$R^{70}$, —$NR^{70}$C(O)$OR^{70}$, —$NR^{70}$C(S)$OR^{70}$, —$NR^{70}$C(O) $NR^{80}R^{80}$, —$NR^{70}$C($NR^{70}$)$R^{70}$ and —$NR^{70}$C($NR^{70}$) $NR^{80}R^{80}$, where $R^{60}$, $R^{70}$, $R^{80}$ and $M^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

As used herein, the term "synthon" refers to a compound that includes a core constituent part of a target molecule to be synthesized that is regarded as the basis of a synthetic procedure. As used herein, the term "synthetic equivalent" refers to a compound that can be utilized as an alternative to a target intermediate or starting material in a synthetic strategy without need for substantively changing the strategy and procedure. It is understood that a synthetic equivalent can be related to the target intermediate or starting material by including the same arrangement of functional groups or precursors thereof, or protected versions thereof, on a fragment of the underlying target scaffold of interest.

"Promoiety" refers to a form of protecting group that, when used to mask a functional group within an active agent, converts the active agent into a prodrug.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like, hydrobromic, hydriodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate (e.g., 3-hexyne-1,6-dioate), benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, 3-hydroxybutyrate, glycollate, maleate, tartrate, methanesulfonate, propanesulfonates, naphthalene-1-sulfonate, naphthalene-2-sulfonate, mandelate, hippurate, gluconate, lactobionate, and the like salts. In certain specific embodiments, pharmaceutically acceptable acid addition salts include those formed with mineral acids such as hydrochloric acid and hydrobromic acid, and those formed with organic acids such as fumaric acid and maleic acid.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or decrease the growth rate of the tumor.

"Patient" refers to human and non-human subjects, especially mammalian subjects.

The term "treating" or "treatment" as used herein means the treating or treatment of a disease or medical condition in a patient, such as a mammal (particularly a human) that includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

Other definitions of terms may appear throughout the specification.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an agent" includes a plurality of such agents and reference to "the agent" includes reference to one or more agents and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides anti-bacterial compounds that are aromatic sulfonyl fluoride agents. The subject aromatic sulfonyl fluoride agents can have a pharmacophore that provides for potent antibacterial activity. As such, the subject agents find use in a variety of antibiotic applications, including in vitro and in vivo applications. In some cases, the subject agents find use in methods of treating bacterial infections in a subject.

In further describing the various aspects of the invention, the function and structure of various embodiments of RAS modulating compounds are described first in greater detail, followed by a description of methods and applications in which the compounds finds use.

Aromatic Sulfonyl Fluoride Agents

Aspects of the present disclosure include aromatic sulfonyl fluoride agents. The term "aromatic sulfonyl fluoride agent" refers to a compound including an aromatic group substituted with a sulfonyl fluoride group, e.g., a —SO$_2$F group. The sulfonyl is an electrophilic group capable of reacting with a biomolecule, e.g., a target protein. The sulfonyl fluoride group of the subject compounds can act as a privileged warhead group to provide an irreversible inhibitor or inactivator compound with low toxicity. In some cases, the reactivity of the sulfonyl fluoride warhead is increased in the presence of a favorable local Hydrogen-bonding environment to provide for selective reaction of the subject compounds with protein targets that provide such a local Hydrogen-bonding environment. The reactivity of sulfonyl fluoride in the context of Click Chemistry is described by Sharpless et al. ("Sulfur(VI) Fluoride Exchange (SuFEx): Another Good Reaction for Click Chemistry" Angew. Chem. Int. Ed. 2014, 53, 9430).

The sulfonyl fluoride group of the subject compounds is attached to an aromatic group. The term aromatic group refers to an aryl or heteroaryl group. Any convenient aromatic groups can be substituted with a sulfonyl fluoride for use in the subject compounds. The aromatic group of the subject compounds can be a sulfonyl fluoride-substituted aryl or sulfonyl fluoride-substituted heteroaryl that is further substituted with an electron withdrawing group at an adjacent position of the aromatic group, in addition to the sulfonyl fluoride group. Aspects of the present disclosure include aromatic sulfonyl fluoride compounds having an electron withdrawing substituent in the 2 position relative to the sulfonyl fluoride warhead group. The positioning of an electron withdrawing group at the 2 position of the subject compound can provide for a desirable reactivity of the sulfonyl fluoride warhead with a target biomolecule. Aromatic sulfonyl fluoride compounds having an electron withdrawing substituent in the 2 position can be effective antibacterial agents. Electron withdrawing groups of interest which can be included in the subject compounds include, but are not limited to, nitro, trifluoromethyl, cyano, sulfonate and ammonium.

In some cases, the aromatic sulfonyl fluoride agent includes a nitro substituent located at an adjacent position (e.g., the 2-position) of the aromatic group relative to the location of the adjacent sulfonyl fluoride group (e.g., the 1-position). In such cases, the aromatic sulfonyl fluoride agent may be referred to as a nitroaromatic sulfonyl fluoride (NSF). It is understood that the numbering convention of aromatic groups of interest can vary and, as such, in the systematic names of particular compounds of interest the formal numbering assignments of the positions of the aromatic group where the sulfonyl fluoride and electron withdrawing groups are attached may be different.

In some cases, the aromatic group is monocyclic. A monocyclic aromatic group can be a 5- or 6-membered aryl or heteroaryl. In certain instances, the aromatic group is bicyclic. A bicyclic aromatic group can be a fused bicyclic group, such as a fused bicyclic group comprising two fused 5- and/or 6-membered carbocyclic or heterocyclic rings. In some cases, the aromatic group is a 5-membered heterocycle (e.g., a heterocycle including one or two N, O and/or S heteroatoms in the 5-membered ring) that is di-substituted with sulfonyl fluoride and electron withdrawing groups at adjacent positions of the ring. Aromatic groups of interest include, but are not limited to, thiophene, furanyl, pyrrole, thiazole, oxazole, imidazole, phenyl, pyridine, benzothiophene and benzofuran.

In some embodiments, the aromatic sulfonyl fluoride agent is described by formula (I):

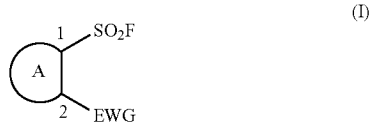

(I)

wherein:

A is an aryl or heteroaryl group (e.g., as described herein) optionally further substituted; and EWG is an electron withdrawing group;

or a pharmaceutically acceptable salt thereof.

In certain instances of formula (I), A is a thiophenyl or substituted thiophenyl. In certain instances of formula (I), A is a furanyl or substituted furanyl. In certain instances of formula (I), A is a pyrrolyl or substituted pyrrolyl. In certain instances of formula (I), A is thiazinyl or substituted thiazinyl. In certain instances of formula (I), A is oxazolyl or substituted oxazolyl. In certain instances of formula (I), A is imidazolyl or substituted imidazolyl. In certain instances of formula (I), A is a phenyl or substituted phenyl. In certain instances of formula (I), A is a pyridyl or substituted pyridyl. In certain instances of formula (I), A is a benzothiophenyl or substituted benzothiophenyl. In certain instances of formula (I), A is a benzofuranyl or substituted benzofuranyl. In certain instances of formula (I), EWG is nitro. In certain instances of formula (I), EWG is —$CF_3$. In certain instances of formula (I), EWG is —CN. In certain instances of formula (I), EWG is —$SO_3H$. In certain instances of formula (I), EWG is —$NR_3^+$ where each R is independently alkyl or substituted alkyl.

In certain instances of formula (I), A is a thiophenyl or substituted thiophenyl and EWG is nitro. In certain instances of formula (I), A is a furanyl or substituted furanyl and EWG is nitro. In certain instances of formula (I), A is a pyrrolyl or substituted pyrrolyl and EWG is nitro. In certain instances of formula (I), A is thiazinyl or substituted thiazinyl and EWG is nitro. In certain instances of formula (I), A is oxazolyl or substituted oxazolyl and EWG is nitro. In certain instances of formula (I), A is imidazolyl or substituted imidazolyl and EWG is nitro. In certain instances of formula (I), A is a phenyl or substituted phenyl and EWG is nitro. In certain instances of formula (I), A is a pyridyl or substituted pyridyl and EWG is nitro. In certain instances of formula (I), A is a benzothiophenyl or substituted benzothiophenyl and EWG is nitro. In certain instances of formula (I), A is a benzofuranyl or substituted benzofuranyl and EWG is nitro.

In certain instances of formula (I), A is a thiophenyl or substituted thiophenyl and EWG is —$CF_3$. In certain instances of formula (I), A is a furanyl or substituted furanyl and EWG is —$CF_3$. In certain instances of formula (I), A is a pyrrolyl or substituted pyrrolyl and EWG is —$CF_3$. In certain instances of formula (I), A is thiazinyl or substituted thiazinyl and EWG is —$CF_3$. In certain instances of formula (I), A is oxazolyl or substituted oxazolyl and EWG is —$CF_3$. In certain instances of formula (I), A is imidazolyl or substituted imidazolyl and EWG is —$CF_3$. In certain instances of formula (I), A is a phenyl or substituted phenyl and EWG is —$CF_3$. In certain instances of formula (I), A is a pyridyl or substituted pyridyl and EWG is —$CF_3$. In certain instances of formula (I), A is a benzothiophenyl or substituted benzothiophenyl and EWG is —$CF_3$. In certain instances of formula (I), A is a benzofuranyl or substituted benzofuranyl and EWG is —$CF_3$.

In certain instances of formula (I), A is a thiophenyl or substituted thiophenyl and EWG is —CN. In certain instances of formula (I), A is a furanyl or substituted furanyl and EWG is —CN. In certain instances of formula (I), A is a pyrrolyl or substituted pyrrolyl and EWG is —CN. In certain instances of formula (I), A is thiazinyl or substituted thiazinyl and EWG is —CN. In certain instances of formula (I), A is oxazolyl or substituted oxazolyl and EWG is —CN. In certain instances of formula (I), A is imidazolyl or substituted imidazolyl and EWG is —CN. In certain instances of formula (I), A is a phenyl or substituted phenyl and EWG is —CN. In certain instances of formula (I), A is a pyridyl or substituted pyridyl and EWG is —CN. In certain instances of formula (I), A is a benzothiophenyl or substituted benzothiophenyl and EWG is —CN. In certain instances of formula (I), A is a benzofuranyl or substituted benzofuranyl and EWG is —CN.

In certain instances of formula (I), A is a thiophenyl or substituted thiophenyl and EWG is —$SO_3H$. In certain instances of formula (I), A is a furanyl or substituted furanyl and EWG is —$SO_3H$. In certain instances of formula (I), A is a pyrrolyl or substituted pyrrolyl and EWG is —$SO_3H$. In certain instances of formula (I), A is thiazinyl or substituted thiazinyl and EWG is —$SO_3H$. In certain instances of formula (I), A is oxazolyl or substituted oxazolyl and EWG is —$SO_3H$. In certain instances of formula (I), A is imidazolyl or substituted imidazolyl and EWG is —$SO_3H$. In certain instances of formula (I), A is a phenyl or substituted phenyl and EWG is —$SO_3H$. In certain instances of formula (I), A is a pyridyl or substituted pyridyl and EWG is —$SO_3H$. In certain instances of formula (I), A is a benzothiophenyl or substituted benzothiophenyl and EWG is —$SO_3H$. In certain instances of formula (I), A is a benzofuranyl or substituted benzofuranyl and EWG is —$SO_3H$.

In certain instances of formula (I), A is a thiophenyl or substituted thiophenyl and EWG is —$NR_3^+$ where each R is independently alkyl or substituted alkyl. In certain instances of formula (I), A is a furanyl or substituted furanyl and EWG is —$NR_3^+$ where each R is independently alkyl or substituted alkyl. In certain instances of formula (I), A is a pyrrolyl or substituted pyrrolyl and EWG is —$NR_3^+$ where each R is independently alkyl or substituted alkyl. In certain instances of formula (I), A is thiazinyl or substituted thiazinyl and EWG is —$NR_3^+$ where each R is independently alkyl or substituted alkyl. In certain instances of formula (I), A is oxazolyl or substituted oxazolyl and EWG is —$NR_3^+$ where each R is independently alkyl or substituted alkyl. In certain instances of formula (I), A is imidazolyl or substituted imidazolyl and EWG is —$NR_3^+$ where each R is independently alkyl or substituted alkyl. In certain instances of formula (I), A is a phenyl or substituted phenyl and EWG is —$NR_3^+$ where each R is independently alkyl or substituted alkyl. In certain instances of formula (I), A is a pyridyl or substituted pyridyl and EWG is —$NR_3^+$ where each R is independently alkyl or substituted alkyl. In certain instances of formula (I), A is a benzothiophenyl or substituted benzothiophenyl and EWG is —NR$_3^+$ where each R is independently alkyl or substituted alkyl. In certain instances of formula (I), A is a benzofuranyl or substituted benzofuranyl and EWG is —NR$_3^+$ where each R is independently alkyl or substituted alkyl.

In some embodiments of formula (I), the aromatic sulfonyl fluoride agent is described by formula (II)

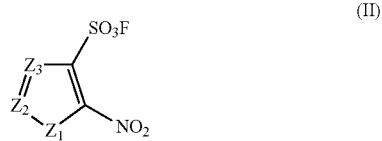

wherein
Z$_1$ is O, S, NR$_5$, CR$_3$═CR$_4$, or CR$_3$═N;
Z$_2$ and Z$_3$ are independently CR$_6$ or N; and
R$_3$, R$_4$, R$_5$ and R$_6$ are independently selected from H, halogen, alkyl, substituted alkyl, alkoxy, substituted alkoxy, aryl, substituted aryl, heteroaryl, substituted heteroaryl, cyano, nitro, hydroxy, carboxy, carboxyamide, sulfonamide and sulfonate;
or a pharmaceutically acceptable salt thereof.

In certain embodiments of formula (II), Z$_1$ is O, S or NR$_5$, and Z$_2$ and Z$_3$ are independently CR$_6$ or N. In certain embodiments of formula (II), Z$_1$ is CR$_3$═CR$_4$, or CR$_3$═N, and Z$_2$ and Z$_3$ are independently CR$_6$ or N. In certain embodiments of formula (II), Z$_1$ is O or S. In certain embodiments of formula (II), R$_3$, R$_4$ and R$_6$ are independently selected from H, halogen, alkyl, substituted alkyl, alkoxy, substituted alkoxy, hydroxy, carboxy, carboxyamide, sulfonamide and sulfonate. In certain embodiments of formula (II), R$_5$ is selected from H, alkyl and substituted alkyl.

In some embodiments of formula (II), the aromatic sulfonyl fluoride agent is described by formula (III)

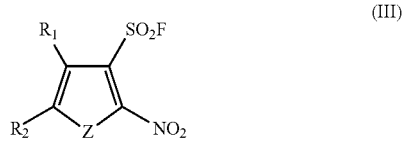

wherein
Z is O, S, NR$_5$, CR$_3$═CR$_4$, CR$_3$═N; and
R$^1$, R$_2$, R$_3$, R$_4$ and R$_5$ are independently selected from H, halogen, alkyl, substituted alkyl, alkoxy, substituted alkoxy, aryl, substituted aryl, heteroaryl, substituted heteroaryl, cyano, nitro, hydroxy, carboxy, carboxyamide, sulfonamide and sulfonate; or a pharmaceutically acceptable salt thereof.

In certain embodiments of formula (III), Z is O or S. In certain embodiments of formula (III), Z is O. In certain embodiments of formula (III), Z is S. In certain embodiments of formula (III), Z is NR$_5$. In some cases, Z is NR$_5$ where R$_5$ is H, alkyl or substituted alkyl. In certain embodiments of formula (III), Z is CR$_3$═CR$_4$. In certain embodiments of formula (III), Z is CR$_3$═CR$_4$, where R$_3$ and R$_4$ are independently H, halogen, alkyl, substituted alkyl, hydroxy, alkoxy or substituted alkoxy. In certain embodiments of formula (III), Z is CR$_3$═N. In certain embodiments of formula (III), Z is CR$_3$═N, where R$_3$ is H, halogen, alkyl, substituted alkyl, alkoxy or substituted alkoxy. In certain embodiments of formula (III), R$_1$ and R$_2$ are independently selected from H, halogen, alkyl, substituted alkyl, alkoxy and substituted alkoxy. In certain embodiments of formula (III), Z is O or S and R$_1$ and R$_2$ are independently selected from H, halogen, alkyl and substituted alkyl. In certain embodiments of formula (III), Z is S and R$_1$ and R$_2$ are independently selected from H, halogen, alkyl and substituted alkyl. In certain cases of formula (III), R$_1$ and R$_2$ are each H.

In certain embodiments of formula (III), the compound is of the structure:

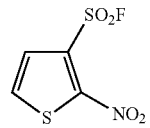

or a pharmaceutically acceptable salt thereof.

Aspects of the present disclosure include compounds that are aromatic sulfonyl fluoride agents, salts thereof (e.g., pharmaceutically acceptable salts), and/or solvate, hydrate and/or prodrug forms thereof. In addition, it is understood that, in any compound described herein having one or more chiral centers, if an absolute stereochemistry is not expressly indicated, then each center may independently be of R-configuration or S-configuration or a mixture thereof. It will be appreciated that all permutations of salts, solvates, hydrates, prodrugs and stereoisomers are meant to be encompassed by the present disclosure.

In some embodiments, the subject compounds, or a prodrug form thereof, are provided in the form of pharmaceutically acceptable salts. Compounds containing an amine or nitrogen containing heteraryl group may be basic in nature and accordingly may react with any number of inorganic and organic acids to form pharmaceutically acceptable acid addition salts. Acids commonly employed to form such salts include inorganic acids such as hydrochloric, hydrobromic, hydriodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycollate, maleate, tartrate, methanesulfonate, propanesulfonates, naphthalene-1-sulfonate, naphthalene-2-sulfonate, mandelate, hippurate, gluconate, lactobionate, and the like salts. In certain specific embodiments, pharmaceutically acceptable acid addition salts include those formed with mineral acids such as hydrochloric acid and hydrobromic acid, and those formed with organic acids such as fumaric acid and maleic acid.

In some embodiments, the subject compounds are provided in a prodrug form. "Prodrug" refers to a derivative of an active agent that requires a transformation within the body to release the active agent. In certain embodiments, the transformation is an enzymatic transformation. Prodrugs are frequently, although not necessarily, pharmacologically inactive until converted to the active agent. "Promoiety" refers to a form of protecting group that, when used to mask a functional group within an active agent, converts the active agent into a prodrug. In some cases, the promoiety will be attached to the drug via bond(s) that are cleaved by enzymatic or non-enzymatic means in vivo. Any convenient prodrug forms of the subject compounds can be prepared, e.g., according to the strategies and methods described by Rautio et al. ("Prodrugs: design and clinical applications", Nature Reviews Drug Discovery 7, 255-270 (February 2008)).

In some embodiments, the subject compounds, prodrugs, stereoisomers or salts thereof are provided in the form of a solvate (e.g., a hydrate). The term "solvate" as used herein refers to a complex or aggregate formed by one or more molecules of a solute, e.g. a prodrug or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

Methods

As summarized above, aspects of the subject methods include administering to a subject in need thereof a therapeutically effective amount of an antibacterial aromatic sulfonyl fluoride agent (e.g., as described herein) effective to treat a bacterial infection in the subject. By "an amount effective to treat infection" is meant the concentration of a compound that is sufficient to elicit the desired biological effect. The subject can be an individual who is infected, or suspected of being infected, with a bacterial pathogen, and may or may not have previously manifested active disease symptoms. Methods for the prevention or treatment of a bacterial infection can be initiated in an individual manifesting active symptoms of disease.

A variety of bacteria and bacterial infections can be targeted for treatment using the subject aromatic sulfonyl fluoride agents in the subject methods. The aromatic sulfonyl fluoride agents of the present disclosure can have broad spectrum anti-bacterial activity.

In some instances, the bacterial infection is an infection with a Gram-negative bacterium. Gram-negative bacteria of interest include, but are not limited to, *Pseudomonas aeruginosa, Escherichia coli, Acinetobacter baumannii* and an Enterobacteriaceae. In some cases, the Gram-negative bacterium is a non-fermenting bacterium. In some cases, the Gram-negative bacterium is an anaerobic bacterium. In some cases, the Gram-negative bacterium is a facultative anaerobic bacterium. In some cases, the Gram-negative bacterium is an aerobic bacterium. Gram-negative bacteria include bacteria from genera comprising any one of *Chlamydia, Pseudomonas, Erwinia, Pantoea, Vibrio, Burkholderia, Ralstonia, Xanthomonas, Salmonella, Shigella, Chromobacterium, Yersinia, Sodalis, Escherichia, Citrobacter, Edwardsiella, Mesorhizobium, Rhizobium, Aeromonas, Photorhabdus, Vibrio, Bordetella,* or *Desulfovibrio*. Non-limiting examples of Gram-negative bacteria include *Chlamydia trachomatis, Chlamydia pneumoniae, Pseudomonas syringae, Erwinia amylovora, Pantoea agglomerans, Vibrio parahaemolyticus, Burkholderia cepacia, Burkholderia pseudomallei, Ralstonia solanacearum, Xanthomonas campestris, Salmonella enterica, Shigella flexneri, Burkholderia pseudomallei, Chromobacterium violaceum, Yersinia enterocolitica, Sodalis glossinidius, Escherichia coli, Salmonella enterica, Citrobacter rodentium, Chromobacterium violaceum, Yersinia pestis, Yersinia pseudotuberculosis, Edwardsiella tarda, Mesorhizobium loti, Rhizobium* sp., *Yersinia pseudotuberculosis, Yersinia enterocolitica, Pseudomonas aeruginosa, Aeromonas salmonicida, Photorhabdus luminescens, Vibrio parahaemolyticus, Bordetella pertussis,* and *Desulfovibrio vulgaris*. Suitable bacteria include non-fermenting Gram-negative bacilli such as bacteria of a genus selected from *Pseudomonas, Alcaligenes*, and *Acitenobacter*.

Suitable enterobacteriaceae include, but are not limited to, bacteria of a genus selected from *Escherichia, Klebsiella, Enterobacter, Proteus, Serratia, Shigella, Citrobacter, Salmonella,* and *Yersinia*. Suitable enterobacteriaceae include, but are not limited to, *Escherichia coli, Klebsiella pneumonia, Enterobacter aerogenes, Enterobacter cloacae, Proteus vulgaris, Shigella flexneri, Serratia marcescens, Citrobacter freundii, Yersinia enterocolitica,* and *Salmonella enteritidis*.

In certain instances, the bacterial infection is an infection with a Gram-positive bacterium. Gram-positive bacteria of interest include, but are not limited to, methicillin-resistant *Staphylococcus aureus*. In some cases, the bacterial infection is an infection with a drug resistant bacterium, such as a carbapenem-resistant bacterium. In some cases, the Gram-positive bacterium is a bacterium of a genus selected from *Streptococcus, Staphylococcus,* and *Bacillus*. Gram-positive bacteria include, but are not limited to, *Staphylococcus aureus, Streptococcus pneumoniae, Enterococcus faecalis, Bacillus anthracis, Staphylococcus epidermidis,* and *Streptococcus pyogenes*.

In some cases, the bacterial infection is an infection with a drug-resistant bacterium. In some cases, the bacterium is methicillin resistant. In some cases, the bacterium is carbapenem resistant. In some cases, the bacterium is a multi-drug resistant bacterium, e.g., a bacterium that is resistant to two or more anti-bacterial agents. In some cases, the bacterium is a drug-resistant bacterium selected from *Staphylococcus aureus, Streptococcus pneumoniae, Clostridium difficile* and *Pseudomonas aeruginosa*.

As used herein, the term "subject" refers to a mammal. Exemplary mammals include, but are not limited to, humans, domestic animals (e.g., a dog, cat, or the like), farm animals (e.g., a cow, a sheep, a pig, a horse, or the like) or laboratory animals (e.g., a monkey, a rat, a mouse, a rabbit, a guinea pig, or the like). In certain embodiments, the subject is human.

As used herein, the terms "treatment," "treating," and the like, refer to obtaining a desired pharmacologic and/or physiological effect. The effect may be prophylactic in terms of completely or partially preventing a disease (e.g., bacterial infection) or symptom thereof and/or may be therapeutic in terms of a partial or complete cure for a disease (e.g., bacterial infection) and/or adverse effect attributable to the disease (e.g., bacterial infection). As used herein, the terms "treating," "treatment," "therapeutic," or "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the patient's overall feeling of well-being or appearance. "Treatment," as used herein, covers any treatment of a disease in a mammal, particularly in a human, and includes: (a) preventing the disease (e.g., bacterial infection) from occurring in a subject which may be predisposed to the disease (e.g., bacterial infection) but has not yet been diagnosed as having it; (b) inhibiting the disease (e.g., bacterial infection), i.e., arresting its development; and (c) relieving the disease (e.g., bacterial infection), i.e., causing regression of the disease (e.g., bacterial infection).

In some cases, a subject method involves administering to an individual in need thereof an effective amount of an aromatic sulfonyl fluoride agent. In some embodiments, an "effective amount" is an amount that, when administered to an individual in one or more doses, in monotherapy or in combination therapy, is effective to reduce bacterial load in the individual by at least about 20% (20% suppression), at least about 30% (30% suppression), at least about 40% (40% suppression), at least about 50% (50% suppression), at least about 60% (60% suppression), at least about 70% (70% suppression), at least about 80% (80% suppression), or at least about 90% (90% suppression), compared to the bacterial load in the individual in the absence of treatment with the antibacterial aromatic sulfonyl fluoride agent.

In some embodiments, an "effective amount" of an aromatic sulfonyl fluoride agent is an amount that, when administered in one or more doses to an individual having a bacterial infection, is effective to achieve a 1.5-log, a 2-log, a 2.5-log, a 3-log, a 3.5-log, a 4-log, a 4.5-log, or a 5-log reduction in bacteria colony formation unit in the serum of the individual.

In some embodiments, an effective amount of an aromatic sulfonyl fluoride agent is an amount that ranges from about 50 ng/ml to about 50 µg/ml (e.g., from about 50 ng/ml to about 40 µg/ml, from about 30 ng/ml to about 20 µg/ml, from about 50 ng/ml to about 10 µg/ml, from about 50 ng/ml to about 1 µg/ml, from about 50 ng/ml to about 800 ng/ml, from about 50 ng/ml to about 700 ng/ml, from about 50 ng/ml to about 600 ng/ml, from about 50 ng/ml to about 500 ng/ml, from about 50 ng/ml to about 400 ng/ml, from about 60 ng/ml to about 400 ng/ml, from about 70 ng/ml to about 300 ng/ml, from about 60 ng/ml to about 100 ng/ml, from about 65 ng/ml to about 85 ng/ml, from about 70 ng/ml to about 90 ng/ml, from about 200 ng/ml to about 900 ng/ml, from about 200 ng/ml to about 800 ng/ml, from about 200 ng/ml to about 700 ng/ml, from about 200 ng/ml to about 600 ng/ml, from about 200 ng/ml to about 500 ng/ml, from about 200 ng/ml to about 400 ng/ml, or from about 200 ng/ml to about 300 ng/ml).

In some embodiments, an effective amount of an aromatic sulfonyl fluoride agent is an amount that ranges from about 10 µg to about 100 mg, e.g., from about 10 µg to about 50 µg, from about 50 µg to about 150 µg, from about 150 µg to about 250 µg, from about 250 µg to about 500 µg, from about 500 µg to about 750 µg, from about 750 µg to about 1 ng, from about 1 ng to about 10 ng, from about 10 ng to about 50 ng, from about 50 ng to about 150 ng, from about 150 ng to about 250 ng, from about 250 ng to about 500 ng, from about 500 ng to about 750 ng, from about 750 ng to about 1 µg, from about 1 µg to about 10 µg, from about 10 µg to about 50 µg, from about 50 µg to about 150 µg, from about 150 kg to about 250 kg, from about 250 kg to about 500 kg, from about 500 kg to about 750 µg, from about 750 kg to about 1 mg, from about 1 mg to about 50 mg, from about 1 mg to about 100 mg, or from about 50 mg to about 100 mg. The amount can be a single dose amount or can be a total daily amount. The total daily amount can range from 10 µg to 100 mg, or can range from 100 mg to about 500 mg, or can range from 500 mg to about 1000 mg.

In some embodiments, a single dose of an aromatic sulfonyl fluoride agent is administered. In other embodiments, multiple doses of an active agent are administered. Where multiple doses are administered over a period of time, the aromatic sulfonyl fluoride agent is administered twice daily (qid), daily (qd), every other day (qod), every third day, three times per week (tiw), or twice per week (biw) over a period of time. For example, an active agent is administered qid, qd, qod, tiw, or biw over a period of from one day to about 2 years or more. For example, an aromatic sulfonyl fluoride agent is administered at any of the aforementioned frequencies for one week, two weeks, one month, two months, six months, one year, or two years, or more, depending on various factors.

Administration of an effective amount of an aromatic sulfonyl fluoride agent to an individual in need thereof can result in one or more of: 1) a reduction in bacterial load; 2) a reduction in bacterial load in a target biological sample; 3) a reduction in the spread of a bacteria from one cell to another cell in an individual; 4) a reduction in bacterial entry into (e.g., reduction of internalization of a bacteria into) a cell; 5) a reduction in time to seroconversion (bacteria undetectable in patient serum); 6) an increase in the rate of sustained response to therapy; 7) a reduction of morbidity or mortality in clinical outcomes; 8) shortening the total length of treatment when combined with other antibacterial agents; and 9) an improvement in an indicator of disease response (e.g., a reduction in one or more symptoms of a bacterial infection, such as fever, etc.).

Any of a variety of methods can be used to determine whether a treatment method is effective. For example, a biological sample obtained from an individual who has been treated with a subject method can be assayed for the presence and/or level of a bacteria-encoded protein, for the presence and/or level of bacteria genomes, and the like.

Methods of measuring bacteria concentration will be known to one of ordinary skill in the art and may include: plaque assay (determine the number of colony forming units (CFU) in a sample by plating a known volume and/or dilution of sample on agar plates and count the number of formed bacterial colonies); fluorescent focus assay (FFA); protein bases assays (e.g., hemagglutination assay, bicinchoninic acid assay, single radial immunodiffusion assay, and the like); transmission Electron Microscopy (TEM); flow cytometry (e.g., using antibodies and/or probes against viral specific proteins and/or nucleic acids); etc.

In some embodiments, the subject methods further include administering one or more additional agents, e.g., antibacterial agents. In certain embodiments, the subject methods include administering a therapeutically effective amount of one or more additional agents selected from the group consisting of isoniazid, rifampin, pyrazinamide, ethambutol, rifabutin, rifapentine, amikacin, capremycin, cycloserine, ethionamide, levofloxacin, moxifloxacin, para-aminosalicylic, nitazoxanide, gleevec, CPZEN-45 and streptomycin. In certain embodiments, the subject methods include administering a therapeutically effective amount of one or more additional agents selected from isoniazid, pyrazinamide and rifampin.

In certain embodiments, the aromatic sulfonyl fluoride agent and the one or more additional agents are administered at the same time. In certain embodiments, the aromatic sulfonyl fluoride agent and the one or more additional agents are administered as separate formulations.

In certain embodiments, the aromatic sulfonyl fluoride agent and the one or more additional agents are administered in a single formulation. In certain embodiments, the aromatic sulfonyl fluoride agent and the one or more additional agents are administered sequentially.

Combination therapy includes administration of a single pharmaceutical dosage formulation which contains the subject aromatic sulfonyl fluoride agent and one or more additional agents; as well as administration of the subject compound and one or more additional agent(s) in its own separate pharmaceutical dosage formulation. For example, a subject aromatic sulfonyl fluoride agent and an additional agent active against an infectious disease (e.g., a bacterial infection) can be administered to the patient together in a single dosage composition such as a combined formulation, or each agent can be administered in a separate dosage formulation. Where separate dosage formulations are used, the subject compound and one or more additional agents can be administered concurrently, or at separately staggered times, e.g., sequentially.

Also provided are methods of inhibiting bacteria in a cell. In some embodiments, the cell is in vitro. In other embodiments, the cell is in vivo. In some embodiments, the method includes contacting a sample comprising a cell with an aromatic sulfonyl fluoride agent (e.g., as described herein). Any convenient methods of contacting a sample with the agent may be utilized.

The cell may in a biological sample. The term "sample" as used herein relates to a material or mixture of materials, typically, although not necessarily, in liquid form, containing one or more analytes of interest. In one embodiment, the term as used in its broadest sense, refers to any plant, animal or bacterial material containing cells or producing cellular metabolites, such as, for example, tissue or fluid isolated from an individual (including without limitation plasma, serum, cerebrospinal fluid, lymph, tears, saliva and tissue sections) or from in vitro cell culture constituents, as well as samples from the environment. The term "sample" may also refer to a "biological sample". As used herein, the term "a biological sample" refers to a whole organism or a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). A "biological sample" can also refer to a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. In certain embodiments, the sample has been removed from an animal or plant. Biological samples of the invention include cells. The term "cells" is used in its conventional sense to refer to the basic structural unit of living organisms, both eukaryotic and prokaryotic, having at least a nucleus and a cell membrane. In certain embodiments, cells include prokaryotic cells, such as from bacteria. In other embodiments, cells include eukaryotic cells, such as cells obtained from biological samples from animals, plants or fungi.

In some embodiments of the method, the aromatic sulfonyl fluoride agent inhibits bacterial replication in a cell. In some cases, the cell is infected with a drug-resistant strain or a multi-drug resistant strain of a bacterium. In certain embodiments of the method, the aromatic sulfonyl fluoride agent inhibits bacterial replication in the cell with an $EC_{80}$ of about 10 μM or less, such as about 3 μM or less, 1 μM or less, 300 nM or less, or 100 nM or less, 30 nM or less or even 10 nM or less.

In some embodiments of the method, the aromatic sulfonyl fluoride agent has a microbicidal activity in a cell infected with a Gram-positive bacterium. In some cases, the cell is infected with a drug-resistant strain or a multi-drug resistant strain of the bacterium. In certain embodiments, the cell is infected with a Methicillin-resistant *Staphylococcus aureus*. In some embodiments of the method, the aromatic sulfonyl fluoride agent has a microbicidal activity in a cell infected with a Gram-negative bacterium. In certain cases, the Gram-negative bacterium is selected from *Pseudomonas aeruginosa, Escherichia coli, Acinetobacter baumannii* and an Enterobacteriaceae. In some cases, the cell is infected with a drug-resistant strain or a multi-drug resistant strain of the bacterium. In certain embodiments, the cell is infected with a Methicillin-resistant *Staphylococcus aureus*. In certain embodiments, the cell is infected with a drug-resistant bacterium, such as a carbapenem-resistant bacterium. The microbicidal activity or potency of the agents may be assayed using any convenient methods, e.g., using a cell based antibacterial assay.

Pharmaceutical Preparations

Also provided are pharmaceutical preparations. Pharmaceutical preparations are compositions that include an aromatic sulfonyl fluoride agent (for example one or more of the subject compounds, either alone or in the presence of one or more additional active agents) present in a pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the present disclosure is formulated for administration to a mammal. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used.

When administered to a mammal, the compounds and compositions of the present disclosure and pharmaceutically acceptable vehicles, excipients, or diluents may be sterile. In some instances, an aqueous medium is employed as a vehicle when the subject compound is administered intravenously, such as water, saline solutions, and aqueous dextrose and glycerol solutions.

Pharmaceutical compositions can take the form of capsules, tablets, pills, pellets, lozenges, powders, granules, syrups, elixirs, solutions, suspensions, emulsions, suppositories, or sustained-release formulations thereof, or any other form suitable for administration to a mammal. In some instances, the pharmaceutical compositions are formulated for administration in accordance with routine procedures as a pharmaceutical composition adapted for oral or intravenous administration to humans. Examples of suitable pharmaceutical vehicles and methods for formulation thereof are described in Remington: The Science and Practice of Pharmacy, Alfonso R. Gennaro ed., Mack Publishing Co. Easton, Pa., 19th ed., 1995, Chapters 86, 87, 88, 91, and 92, incorporated herein by reference. The choice of excipient will be determined in part by the particular compound, as well as by the particular method used to administer the composition. Accordingly, there is a wide variety of suitable formulations of the subject pharmaceutical compositions.

Administration of the subject compounds may be systemic or local. In certain embodiments administration to a mammal will result in systemic release of a compound of the present disclosure (for example, into the bloodstream). Methods of administration may include enteral routes, such as oral, buccal, sublingual, and rectal; topical administration, such as transdermal and intradermal; and parenteral administration. Suitable parenteral routes include injection via a hypodermic needle or catheter, for example, intravenous, intramuscular, subcutaneous, intradermal, intraperitoneal, intraarterial, intraventricular, intrathecal, and intracameral injection and non-injection routes, such as intravaginal rectal, or nasal administration. In certain embodiments, the compounds and compositions of the present disclosure are administered subcutaneously. In certain embodiments, the compounds and compositions of the present disclosure are administered orally. In certain embodiments, it may be desirable to administer one or more compounds of the present disclosure locally to the area in need of treatment. This may be achieved, for example, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

The compounds can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

A subject compound may also be formulated for oral administration. For an oral pharmaceutical formulation, suitable excipients include pharmaceutical grades of carriers such as mannitol, lactose, glucose, sucrose, starch, cellulose, gelatin, magnesium stearate, sodium saccharine, and/or magnesium carbonate. For use in oral liquid formulations, the composition may be prepared as a solution, suspension, emulsion, or syrup, being supplied either in solid or liquid form suitable for hydration in an aqueous carrier, such as, for example, aqueous saline, aqueous dextrose, glycerol, or ethanol, preferably water or normal saline. If desired, the composition may also contain minor amounts of non-toxic auxiliary substances such as wetting agents, emulsifying agents, or buffers. In some embodiments, formulations suitable for oral administration can include (a) liquid solutions, such as an effective amount of the compound dissolved in diluents, such as water, or saline; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can include the active ingredient in a flavor, usually sucrose and acacia or tragacanth, as well as pastilles including the active ingredient in an inert base, such as gelatin and glycerin, or sucrose and acacia, emulsions, gels, and the like containing, in addition to the active ingredient, such excipients as are described herein.

The subject formulations can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

In some embodiments, formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for topical administration may be presented as creams, gels, pastes, or foams, containing, in addition to the active ingredient, such carriers as are appropriate. In some embodiments the topical formulation contains one or more components selected from a structuring agent, a thickener or gelling agent, and an emollient or lubricant. Frequently employed structuring agents include long chain alcohols, such as stearyl alcohol, and glyceryl ethers or esters and oligo(ethylene oxide) ethers or esters thereof. Thickeners and gelling agents include, for example, polymers of acrylic or methacrylic acid and esters thereof, polyacrylamides, and naturally occurring thickeners such as agar, carrageenan, gelatin, and guar gum. Examples of emollients include triglyceride esters, fatty acid esters and amides, waxes such as beeswax, spermaceti, or carnauba wax, phospholipids such as lecithin, and sterols and fatty acid esters thereof. The topical formulations may further include other components, e.g., astringents, fragrances, pigments, skin penetration enhancing agents, sunscreens (e.g., sunblocking agents), etc.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may include the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present disclosure calculated in an amount sufficient to produce the desired effect in association with a pharmaceutically acceptable diluent, carrier or vehicle. The specifications for the novel unit dosage forms of the present disclosure depend on the particular compound employed and the effect to be achieved, and the pharmacodynamics associated with each compound in the host. In pharmaceutical dosage forms, the compounds may be administered in the form of a free base, their pharmaceutically acceptable salts, or they may also be used alone or in appropriate association, as well as in combination, with other pharmaceutically active compounds.

Dose levels can vary as a function of the specific compound, the nature of the delivery vehicle, and the like. Desired dosages for a given compound are readily determinable by a variety of means. The dose administered to an animal, particularly a human, in the context of the present disclosure should be sufficient to effect a prophylactic or therapeutic response in the animal over a reasonable time frame, e.g., as described in greater detail herein. Dosage will depend on a variety of factors including the strength of the particular compound employed, the condition of the animal, and the body weight of the animal, as well as the severity of the illness and the stage of the disease. The size of the dose will also be determined by the existence, nature, and extent of any adverse side-effects that might accompany the administration of a particular compound.

Kits

Also provided are kits that include aromatic sulfonyl fluoride agents of the present disclosure. The subject kits can include one or more dosages of the aromatic sulfonyl fluoride agent, and optionally one or more dosages of one or more additional active agents (e.g., antibacterial agents). Conveniently, the formulations may be provided in a unit dosage format. In such kits, in addition to the containers containing the formulation(s), e.g. unit doses, is an informational package insert describing the use of the subject formulations in the methods of the invention, e.g., instructions for using the subject unit doses to treat infectious disease such as a bacterial infection.

In some embodiments, the kit includes an aromatic sulfonyl fluoride agent (e.g., as described herein) and at least one additional compound is selected from isoniazid, rifampin, pyrazinamide, ethambutol, rifabutin, rifapentine, amikacin, capremycin, cycloserine, ethionamide, levofloxacin, moxifloxacin, para-aminosalicylic, nitazoxanide, gleevec, CPZEN-45 and streptomycin. In certain embodiments, the kit includes one or more additional compounds selected from isoniazid, pyrazinamide and rifampin.

In addition to the above-mentioned components, a subject kits may further include instructions for using the components of the kit, e.g., to practice the subject method. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, Hard Disk Drive (HDD), portable flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Utility

The agents, compositions and methods of the present disclosure, e.g., as described above, find use in a variety of applications. Applications of interest include, but are not limited to: therapeutic applications, research applications, and diagnostic applications.

The subject compounds find use in a variety of therapeutic applications. Therapeutic and diagnostic applications of interest include those applications in which diagnosis and/or treatment of a bacterial infection, are of interest.

Accordingly, in some cases, the methods comprise administering to the mammalian host in need thereof a pharmaceutical composition as described above. As such, the pharmaceutical compositions of the invention are used in methods for treating or preventing particular diseases, e.g., a bacterial infection. The methods comprise, for example, administering to the mammalian host in need thereof a therapeutically-effective amount of a pharmaceutical composition as described above. In some embodiments, the subject compounds may be administered in combination with one or more additional compounds or therapies, including a second target-binding molecule, an antibacterial agent, surgery, catheter devices, and radiation. Combination therapy includes administration of a single pharmaceutical dosage formulation which contains the subject compound and one or more additional agents; as well as administration of the subject compound and one or more additional agent(s) in its own separate pharmaceutical dosage formulation. For example, a subject compound and an additional agent active against an infectious disease (e.g., a bacterial infection) can be administered to the patient together in a single dosage composition such as a combined formulation, or each agent can be administered in a separate dosage formulation. Where separate dosage formulations are used, the subject compound and one or more additional agents can be administered concurrently, or at separately staggered times, e.g., sequentially.

The subject compounds and methods find use in a variety of research applications. The subject compounds and methods may be used to analyze the roles of chloroquine agents in modulating various biological processes involved with a bacterium.

EXAMPLES OF NON-LIMITING ASPECTS OF THE DISCLOSURE

Aspects, including embodiments, of the present subject matter described above may be beneficial alone or in combination, with one or more other aspects or embodiments. Without limiting the foregoing description, certain non-limiting aspects of the disclosure numbered 1-26 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A method of treating a bacterial infection, the method comprising administering to a subject in need thereof a therapeutically effective amount of an antibacterial aromatic sulfonyl fluoride agent.

Aspect 2. The method of aspect 1, wherein the aromatic sulfonyl fluoride agent is a compound of formula (I):

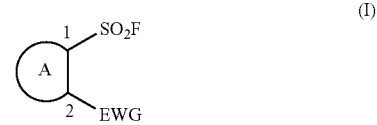

wherein:

A is an aryl or heteroaryl group optionally further substituted; and

EWG is an electron withdrawing group;

or a pharmaceutically acceptable salt thereof.

Aspect 3. The method of aspect 1 or aspect 2, wherein the aromatic sulfonyl fluoride agent is a compound of formula (II):

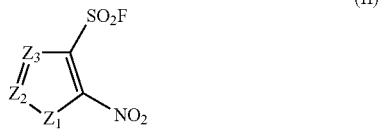

wherein:
Z1 is O, S, NR5, CR3═CR4, or CR3═N;
Z2 and Z3 are independently CR6 or N; and
R3, R4, R5 and R6 are independently selected from H, halogen, alkyl, substituted alkyl, alkoxy, substituted alkoxy, aryl, substituted aryl, heteroaryl, substituted heteroaryl, cyano, nitro, hydroxy, carboxy, carboxyamide, sulfonamide and sulfonate;
or a pharmaceutically acceptable salt thereof.

Aspect 4. The method of any one of aspects 1-3, wherein the aromatic sulfonyl fluoride agent is a compound of formula (III):

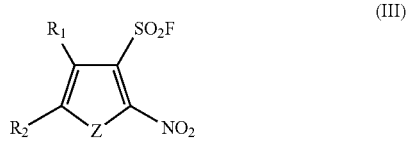

wherein:
Z is O, S, NR5, CR3═CR4, CR3═N; and
R1, R2, R3, R4 and R5 are independently selected from H, halogen, alkyl, substituted alkyl, alkoxy, substituted alkoxy, aryl, substituted aryl, heteroaryl, substituted heteroaryl, cyano, nitro, hydroxy, carboxy, carboxyamide, sulfonamide and sulfonate;
or a pharmaceutically acceptable salt thereof.

Aspect 5. The method of aspect 4, wherein Z is O or S.
Aspect 6. The method of any one of aspects 1-5, wherein the compound has the formula:

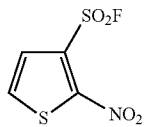

or a pharmaceutically acceptable salt thereof.

Aspect 7. The method of any one of aspects 1-6, wherein the aromatic sulfonyl fluoride agent has broad spectrum anti-bacterial activity.
Aspect 8. The method of any one of aspects 1-7, wherein the bacterial infection is an infection with a Gram-negative bacterium.
Aspect 9. The method of aspect 8, wherein the Gram-negative bacterium is selected from *Pseudomonas aeruginosa, Escherichia coli, Acinetobacter baumannii* and an Enterobacteriaceae.
Aspect 10. The method of any one of aspects 1-7, wherein the bacterial infection is an infection with a Gram-positive bacterium.

Aspect 11. The method of aspect 10, wherein the Gram-positive bacterium is methicillin-resistant *Staphylococcus aureus*.
Aspect 12. The method of any one of aspects 1-11, wherein the bacterial infection comprises an infection with a drug resistant bacterium.
Aspect 13. The method of aspect 12, wherein drug-resistant bacterium is a carbapenem-resistant bacterium.
Aspect 14. The method of any one of aspects 1-13, further comprising administering a therapeutically effective amount of one or more additional agents selected from the group consisting of isoniazid, rifampin, pyrazinamide and ethambutol, rifabutin, rifapentine, amikacin, capremycin, cycloserine, ethionamide, levofloxacin, moxifloxacin, para-aminosalicylic, nitazoxanide, gleevec, CPZEN-45 and streptomycin.
Aspect 15. The method of aspect 14, wherein the antibacterial aromatic sulfonyl fluoride agent and the one or more additional agents are administered substantially simultaneously.
Aspect 16. The method of aspect 14 or aspect 15, wherein the antibacterial aromatic sulfonyl fluoride agent and the one or more additional agents are administered in a single formulation.
Aspect 17. The method of aspect 14, wherein the antibacterial aromatic sulfonyl fluoride agent and the one or more additional agents are administered sequentially.
Aspect 18. The method of aspect 14, wherein the antibacterial aromatic sulfonyl fluoride agent and the one or more additional agents are administered as separate formulations.
Aspect 19. A pharmaceutical composition for treating a bacterial infection in a subject, comprising: a) a therapeutically effective amount of an antibacterial aromatic sulfonyl fluoride active agent; and b) a pharmaceutically acceptable excipient.
Aspect 20. The pharmaceutical composition of aspect 19, wherein the antibacterial aromatic sulfonyl fluoride active agent is a compound of formula (III):

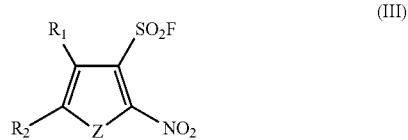

wherein:
Z is O, S, NR5, CR3═CR4, CR3═N; and
R1, R2, R3, R4 and R5 are independently selected from H, halogen, alkyl, substituted alkyl, alkoxy, substituted alkoxy, aryl, substituted aryl, heteroaryl, substituted heteroaryl, cyano, nitro, hydroxy, carboxy, carboxyamide, sulfonamide and sulfonate;
or a pharmaceutically acceptable salt thereof.

Aspect 21. The pharmaceutical composition of any one of aspects 19-20, wherein the antibacterial aromatic sulfonyl fluoride active agent has the structure:

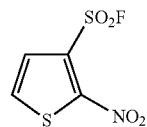

or a pharmaceutically acceptable salt thereof.

Aspect 22. The pharmaceutical composition of any one of aspects 19-21, further comprising a therapeutically effective amount of one or more additional agents selected from the group consisting of isoniazid, rifampin, pyrazinamide, ethambutol, rifabutin, rifapentine, amikacin, capremycin, cycloserine, ethionamide, levofloxacin, moxifloxacin, para-aminosalicylic, nitazoxanide, gleevec, CPZEN-45 and streptomycin.

Aspect 23. A compound having the formula:

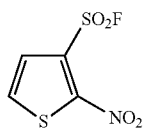

Aspect 24. A kit for treating a bacterial infection in a subject, comprising:

a) a therapeutically effective amount of an antibacterial aromatic sulfonyl fluoride active agent; and b) one or more additional agents selected from the group consisting of isoniazid, rifampin, pyrazinamide and ethambutol, rifabutin, rifapentine, amikacin, capremycin, cycloserine, ethionamide, levofloxacin, moxifloxacin, para-aminosalicylic, nitazoxanide, gleevec, CPZEN-45 and streptomycin.

Aspect 25. The kit of aspect 24, wherein the antibacterial aromatic sulfonyl fluoride active agent is a compound of formula (III):

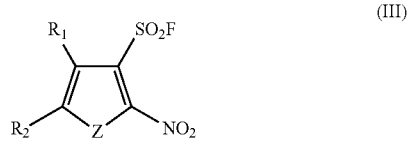

wherein:

Z is O, S, NR5, CR3═CR4, CR3═N; and

R1, R2, R3, R4 and R5 are independently selected from H, halogen, alkyl, substituted alkyl, alkoxy, substituted alkoxy, aryl, substituted aryl, heteroaryl, substituted heteroaryl, cyano, nitro, hydroxy, carboxy, carboxyamide, sulfonamide and sulfonate;

or a pharmaceutically acceptable salt thereof.

Aspect 26. The kit of aspect 24 or aspect 25, wherein the antibacterial aromatic sulfonyl fluoride active agent and the one or more additional agents are in separate containers.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Synthesis and Assessment of Nitrosulfonyl Fluoride Compounds (NSFs)

The experiments focus on development of sulfonyl fluoride-based compounds as antibiotics. The sulfonyl fluorides were selected as pharmacophores for antibiotic development because of their low reactivity to nucleophiles and water. In addition, the electrophilicity of the sulfonyl fluorides is dramatically increased in the presence of local H-bonding and this allows sulfonyl fluoride compounds to selectively react with protein targets that provide the correct local H-bonding environment. Sulfonyl fluorides are thus privileged warheads and have the potential to generate irreversible inhibitors with low toxicity. Sulfonyl fluorides have not previously been investigated as therapeutics or as antibiotics.

The goal of these experiments was to demonstrate that nitrosulfonyl fluoride compounds (NSFs) can provide a new pharmacophore for developing antibiotics. Described herein is a new class of antibiotics composed of aromatic sulfonyl fluorides with a 2-nitro substitution (termed nitrosulfonyl fluorides or NSFs). NSFs have several properties that make them ideal pharmacophores for antibiotic development. Preliminary experiments with selected NSFs show growth inhibition of several drug-resistant GNBs such as Pseudomonas aeruginosa, Escherichia coli, and Acinetobacter baumannii, with MICs in the 1-40 µg/mL range and no mammalian cell toxicity up to 290 µM against RAW 264.7 cells (Table 1). NSFs are exceptionally atom economical with molecular weights between 250-300 g/mol, which is desirable for membrane permeability, and allows significant room for further improvement via chemical modifications. The NSFs are also covalent inhibitors with the potential to be active against dormant bacteria, and have the appropriate log P and molecular weight to be both orally active and permeable to the blood brain barrier.

These results show that NSFs are active against a variety of gram-negative bacteria, and are also active against the gram-positive bacteria, Methicillin-resistant Staphylococcus aureus (MRSA). In addition, it is demonstrated that the antibacterial effects of the NSFs are mediated through a nitroreductase-mediated mechanism, similar to nitrofurantoin and metronidazole. Collectively, these experiments indicate that NSFs can be used to treat bacterial infections in vivo with a wide therapeutic window and represent a new pharmacophore for developing antibiotics against gram-negative bacteria.

NSFs are Active Against GNB and MRSA.

Sulfonyl fluorides are of interest as antibacterial agents because of their ability to selectively react with protein targets. A series of sulfonyl fluorides were investigated for anti-bacterial activity against E. coli. It was observed that aromatic sulfonyl fluorides with a nitro substituent in the 2 position were effective antibacterial agents. A variety of other NSF compounds were then synthesized and assessed to identify a thiophene-based NSF (TNSF) as a lead compound with desirable activity. The TNSF compound was active against a variety of E. coli species and demonstrated activity against A. baumannii and P. aeruginosa, and in several cases had better antibacterial activity than nitrofurantoin. For example, the MIC of TNSF 1 was between 1-5 μg/mL against MRSA and E. coli (ATCC 25922), whereas nitrofurantoin 7 had an MIC of 5-12 μg/mL against these two strains. Thus, introducing a nitro group in the 2 position of an aromatic sulfonyl fluoride compound dramatically improved antibacterial activity, and provided a lead compound fragment for drug development.

study with the E. coli BW25113 library are shown in Table 2 and demonstrate that inactivation of nitroreductase A confers protection against our first-generation NSF, 2-nitrobenzene sulfonyl fluoride 6. Antibiotics such as metronidazole and nitrofurantoin also function via a nitroreductase-mediated mechanism, in which the nitroreductase generates

TABLE 1

Activity of NSFs of interest against GNBs and MRSA.

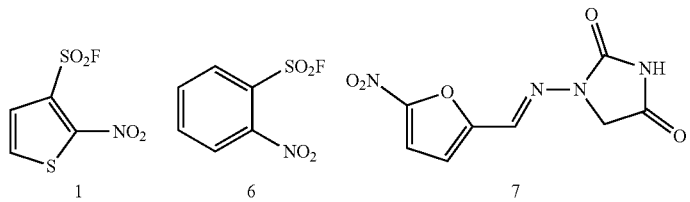

| Pathogens | | MICs (μg/mL) | |
| --- | --- | --- | --- |
| | 1 | 6 | 7 |
| E. coli (KAN) | 0.66 | 5.2 | 0.37 |
| E. coli (AMP) | 10.6 | 21 | 6.0 |
| E. coli SFGH 207 | 42 | 128 | 6.0 |
| E. coli ATCC25922 | 1.32 | 64 | 3.0 |
| MRSA | 5.28 | 128 | 12 |
| A. baumannii (Sensitive) | 21 | >82 | >95 |
| A. baumannii (Resistant) | 42 | >82 | >95 |
| P. aeruginosa SFGH 266 | 42 | >82 | >95 |
| P. aeruginosa SFGH 427 | 84 | >82 | >95 |

Synthesis of TNSF.

Figure 2:
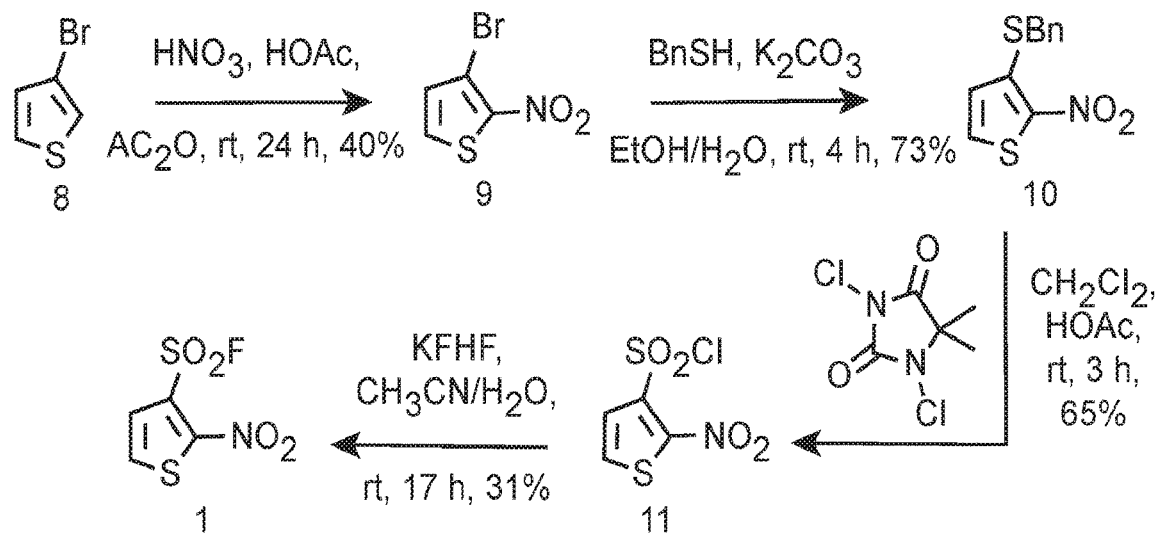
FIG. 2 shows a scheme for the synthesis of 2-nitrothiophene-3-sulfonyl fluoride (compound 1).

The synthetic route to compound 1 is described in FIG. 2 and was accomplished in five overall steps with satisfactory yields. TNSF 1 was purified via column chromatography as a white solid. $^1$H NMR (400 MHz, CDCl$_3$) δ 7.58-7.59 (d, 1H, J=5.68 Hz), 7.69-7.70 (d, 1H, J=5.6 Hz); $^{19}$F NMR (400 MHz, CDCl$_3$) δ 63.7; HRMS (ESI) m/z calculated for Chemical Formula C$_4$H$_2$FNO$_4$S$_2$: 210.9409. Found: 210.9411 (Δ=0.95 ppm).

The Antibacterial Activity of the NSFs is Mediated Via a Nitroreductase-Based Mechanism.

The mechanism by which the NSFs kill bacteria most likely involves covalent modification of protein targets within a cell, given their sulfonyl fluoride functionality. To gain insight into the antibacterial mechanism of the NSFs, the E. coli BW25113 library was incubated with a first-generation NSF, 2-nitrobenzene sulfonyl fluoride 6 and analyzed the bacteria that were resistant to this compound. The BW25113 library contained E. coli that have been transfected with a transposon library, and each bacterial clone in this library have a single gene inactivated by transposon insertion. After NSF treatment of the BW25113 library we then used random barcode transposon-site sequencing (RB-TnSeq) ((Wetmore, K. M., et al. Rapid Quantification of Mutant Fitness in Diverse Bacteria by Sequencing Randomly Bar-Coded Transposons. Mbio 6 (2015)), to identify genes that confer NSF resistance in E. coli (Deutschbauer, A., et al. Towards an Informative Mutant Phenotype for Every Bacterial Gene. J. Bacteriol. 196, 3643-3655 (2014)) to better understand the NSF mechanism of action.

For each BarSeq experiment, genes were identified with significant phenotypes using a t-like statistic that takes into account the consistency of the fitness of all the mutants of that gene. (Wetmore 2015). Genes with |t| of >4 have highly significant phenotypes that are largely reproducible in biological replicate experiments. The results of this phenotype reactive intermediates that damage a variety of important cellular biomolecules, such as ribosomes and metabolic enzymes. The NSFs therefore potentially work via a mechanism similar to metronidazole or nitrofurantoin, except that they probably react with their target biomolecule first and subsequently undergo nitroreductase-mediated activation to an intermediate that then destroys the biomolecule they are conjugated to.

TABLE 2

Mutant fitness profiling

| | Gene Mutation Name | 2-nitrobenzene sulfonyl fluoride |
| --- | --- | --- |
| 1 | Nitroreductase A, NADPH-dependent, FMN-dependent | 6.25 |
| 2 | Multiple antibiotic resistance; transcriptional activator of defense systems | 4.36 |
| 3 | DNA-binding transcriptional repressor | 3.53 |
| 4 | b0912 integration host factor subunit beta | 3.05 |
| 5 | b1217 cation transport regulator | 3.02 |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating a bacterial infection, the method comprising administering to a subject in need thereof a therapeutically effective amount of an antibacterial aromatic sulfonyl fluoride agent, wherein the aromatic sulfonyl fluoride agent is a compound of formula (II):

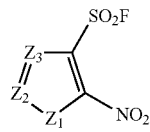

wherein
  $Z_1$ is O or S;
  $Z_2$ and $Z_3$ are independently $CR_6$ or N; and
  $R_3$, $R_4$, $R_5$ and $R_6$ are independently selected from H, halogen, alkyl, substituted alkyl, alkoxy, substituted alkoxy, aryl, substituted aryl, heteroaryl, substituted heteroaryl, cyano, nitro, hydroxy, carboxy, carboxyamide, sulfonamide and sulfonate;
or a pharmaceutically acceptable salt thereof.

2. The method of claim 1, wherein the aromatic sulfonyl fluoride agent is a compound of formula (III):

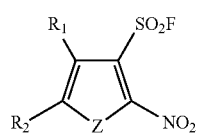

wherein
  Z is O or S; and
  $R_1$ and $R_2$ are independently selected from H, halogen, alkyl, substituted alkyl, alkoxy, substituted alkoxy, aryl, substituted aryl, heteroaryl, substituted heteroaryl, cyano, nitro, hydroxy, carboxy, carboxyamide, sulfonamide and sulfonate;
or a pharmaceutically acceptable salt thereof.

3. The method of claim 1, wherein the compound has the formula:

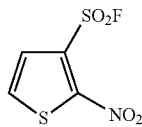

or a pharmaceutically acceptable salt thereof.

4. The method of claim 1, wherein the aromatic sulfonyl fluoride agent has broad spectrum anti-bacterial activity.

5. The method of claim 1, wherein the bacterial infection is an infection with a Gram-negative bacterium.

6. The method of claim 5, wherein the Gram-negative bacterium is selected from *Pseudomonas aeruginosa, Escherichia coli, Acinetobacter baumannii* and an Enterobacteriaceae.

7. The method of claim 1, wherein the bacterial infection is an infection with a Gram-positive bacterium.

8. The method of claim 7, wherein the Gram-positive bacterium is methicillin-resistant *Staphylococcus aureus.*

9. The method of claim 1, wherein the bacterial infection comprises an infection with a drug resistant bacterium.

10. The method of claim 9, wherein the drug-resistant bacterium is a carbapenem-resistant bacterium.

11. The method of claim 1, further comprising administering a therapeutically effective amount of one or more additional agents selected from the group consisting of isoniazid, rifampin, pyrazinamide and ethambutol, rifabutin, rifapentine, amikacin, capremycin, cycloserine, ethionamide, levofloxacin, moxifloxacin, para-aminosalicylic, nitazoxanide, gleevec, CPZEN-45 and streptomycin.

12. The method of claim 11, wherein the antibacterial aromatic sulfonyl fluoride agent and the one or more additional agents are administered substantially simultaneously or sequentially.

13. A pharmaceutical composition for treating a bacterial infection in a subject, comprising: a therapeutically effective amount of an antibacterial aromatic sulfonyl fluoride active agent; and a pharmaceutically acceptable excipient, wherein the antibacterial aromatic sulfonyl fluoride active agent is a compound of formula (III):

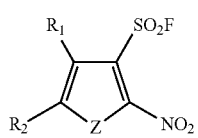

wherein
  Z is O or S; and
  $R_1$ and $R_2$ are independently selected from H, halogen, alkyl, substituted alkyl, alkoxy, substituted alkoxy, aryl, substituted aryl, heteroaryl, substituted heteroaryl, cyano, nitro, hydroxy, carboxy, carboxyamide, sulfonamide and sulfonate;
or a pharmaceutically acceptable salt thereof.

14. The pharmaceutical composition of claim 13, wherein the antibacterial aromatic sulfonyl fluoride active agent has the structure:

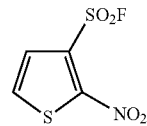

or a pharmaceutically acceptable salt thereof.

15. The pharmaceutical composition of claim 13, further comprising a therapeutically effective amount of one or more additional agents selected from the group consisting of isoniazid, rifampin, pyrazinamide, ethambutol, rifabutin, rifapentine, amikacin, capremycin, cycloserine, ethionamide, levofloxacin, moxifloxacin, para-aminosalicylic, nitazoxanide, gleevec, CPZEN-45 and streptomycin.

16. A kit for treating a bacterial infection in a subject, comprising:
  a therapeutically effective amount of an antibacterial aromatic sulfonyl fluoride active agent; and one or more additional agents selected from the group consisting of isoniazid, rifampin, pyrazinamide and ethambutol, rifabutin, rifapentine, amikacin, capremycin, cycloserine, ethionamide, levofloxacin, moxifloxacin, para-aminosalicylic, nitazoxanide, gleevec, CPZEN-45 and streptomycin, wherein the antibacterial aromatic sulfonyl fluoride active agent is a compound of formula (III):

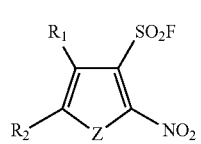
(III)
wherein
Z is O or S; and
R$_1$ and R$_2$ are independently selected from H, halogen, alkyl, substituted alkyl, alkoxy, substituted alkoxy, aryl, substituted aryl, heteroaryl, substituted heteroaryl, cyano, nitro, hydroxy, carboxy, carboxyamide, sulfonamide and sulfonate; or a pharmaceutically acceptable salt thereof.
\* \* \* \* \*

UNITED STATES PATENT AND TRADEMARK OFFICE
CERTIFICATE OF CORRECTION

PATENT NO.           : 11,446,279 B2                  Page 1 of 1
APPLICATION NO.      : 16/618952
DATED                : September 20, 2022
INVENTOR(S)          : Niren Murthy et al.

It is certified that error appears in the above-identified patent and that said Letters Patent is hereby corrected as shown below:

In the Specification

In Column 1, Line 16, please delete "All 17064" and replace it with -- AI117064 --;

In Column 11, Line 63, please delete "3-hydroxybutyrate" and replace it with
-- β-hydroxybutyrate --;

In Column 17, formula (II) please delete "SO₃F" and replace it with -- SO₂F --

So it shows as 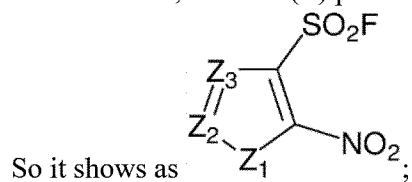 ;

In Column 21, Lines 55 and 56, please delete all "kg" and replace it with -- μg --; and In Column 32, Line 7, please delete "Nitrosulfonvl" and replace it with -- Nitrosulfonyl --.

Signed and Sealed this
Seventh Day of February, 2023

Katherine Kelly Vidal
*Director of the United States Patent and Trademark Office*